(12) United States Patent
Chudzik et al.

(10) Patent No.: US 8,298,157 B2
(45) Date of Patent: Oct. 30, 2012

(54) INTRODUCER CANNULA HAVING A TISSUE ANCHOR FOR USE WITH A MEDICAL INSTRUMENT

(75) Inventors: Rafal Chudzik, Peoria, AZ (US); Angela K. Jensen, Mesa, AZ (US); Jason G. Seiger, Gilbert, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 325 days.

(21) Appl. No.: 12/638,194

(22) Filed: Dec. 15, 2009

(65) Prior Publication Data
US 2011/0144533 A1 Jun. 16, 2011

(51) Int. Cl.
*A61B 10/00* (2006.01)
(52) U.S. Cl. ........................................... 600/567
(58) Field of Classification Search .......... 600/562–568; 606/1, 198; 604/105, 164.11
See application file for complete search history.

(56) References Cited

U.S. PATENT DOCUMENTS

| | | | |
|---|---|---|---|
| 3,844,272 A | 10/1974 | Banko | |
| RE33,258 E | 7/1990 | Onik et al. | |
| 5,330,501 A * | 7/1994 | Tovey et al. | 606/198 |
| 5,526,822 A | 6/1996 | Burbank et al. | |
| 5,601,585 A | 2/1997 | Banik et al. | |
| 5,769,086 A | 6/1998 | Ritchart et al. | |
| 5,795,308 A | 8/1998 | Russin | |
| 5,830,219 A | 11/1998 | Bird et al. | |
| 5,928,164 A | 7/1999 | Burbank et al. | |
| 6,086,544 A | 7/2000 | Hibner et al. | |
| 6,120,462 A | 9/2000 | Hibner et al. | |
| 6,273,862 B1 | 8/2001 | Privitera et al. | |
| 6,312,429 B1 | 11/2001 | Burbank et al. | |
| 6,331,166 B1 | 12/2001 | Burbank et al. | |
| 6,383,145 B1 | 5/2002 | Worm et al. | |
| 6,428,487 B1 | 8/2002 | Burdorff et al. | |
| 6,540,695 B1 | 4/2003 | Burbank et al. | |
| 6,585,664 B2 | 7/2003 | Burdorff et al. | |
| 6,589,252 B2 | 7/2003 | McGuckin, Jr. | |
| 6,659,105 B2 | 12/2003 | Burbank et al. | |
| 6,679,851 B2 | 1/2004 | Burbank et al. | |
| 6,716,179 B2 | 4/2004 | Burbank et al. | |
| 6,752,768 B2 | 6/2004 | Burdorff et al. | |
| 6,758,855 B2 | 7/2004 | Fulton, III et al. | |
| 7,150,712 B2 | 12/2006 | Buehlmann et al. | |
| 7,153,274 B2 | 12/2006 | Stephens et al. | |
| 7,189,206 B2 | 3/2007 | Quick et al. | |
| 7,226,424 B2 | 6/2007 | Ritchart et al. | |
| 7,311,673 B2 | 12/2007 | Mueller, Jr. et al. | |

(Continued)

FOREIGN PATENT DOCUMENTS

GB 2018601 A 10/1979

*Primary Examiner* — Brian Szmal

(57) ABSTRACT

An introducer cannula configured for receiving a medical instrument includes a cannula tube having a side wall surrounding a central lumen, a proximal end, and a distal end. An elongate tissue anchor is positioned in the central lumen of the cannula tube. The elongate tissue anchor has a mounting end and an anchoring free end. The elongate tissue anchor is movable in the central lumen such that the anchoring free end is movable between a retracted position and a deployed position. An actuator is coupled to the proximal end of the cannula tube. The actuator is coupled to the mounting end of the elongate tissue anchor. The actuator is operatively configured to selectively position the anchoring free end of the elongate tissue anchor in one of the retracted position and the deployed position.

21 Claims, 6 Drawing Sheets

U.S. PATENT DOCUMENTS

| | | |
|---|---|---|
| 7,347,829 B2 | 3/2008 | Mark et al. |
| 7,351,211 B2 | 4/2008 | Buehlmann et al. |
| 7,377,902 B2 | 5/2008 | Burbank et al. |
| 7,438,693 B2 | 10/2008 | Vetter et al. |
| 7,479,152 B2 | 1/2009 | Fulton, III et al. |
| 7,648,466 B2 | 1/2010 | Stephens et al. |
| 2005/0113716 A1 | 5/2005 | Mueller, Jr. et al. |
| 2008/0154151 A1 | 6/2008 | Ritchart et al. |

\* cited by examiner

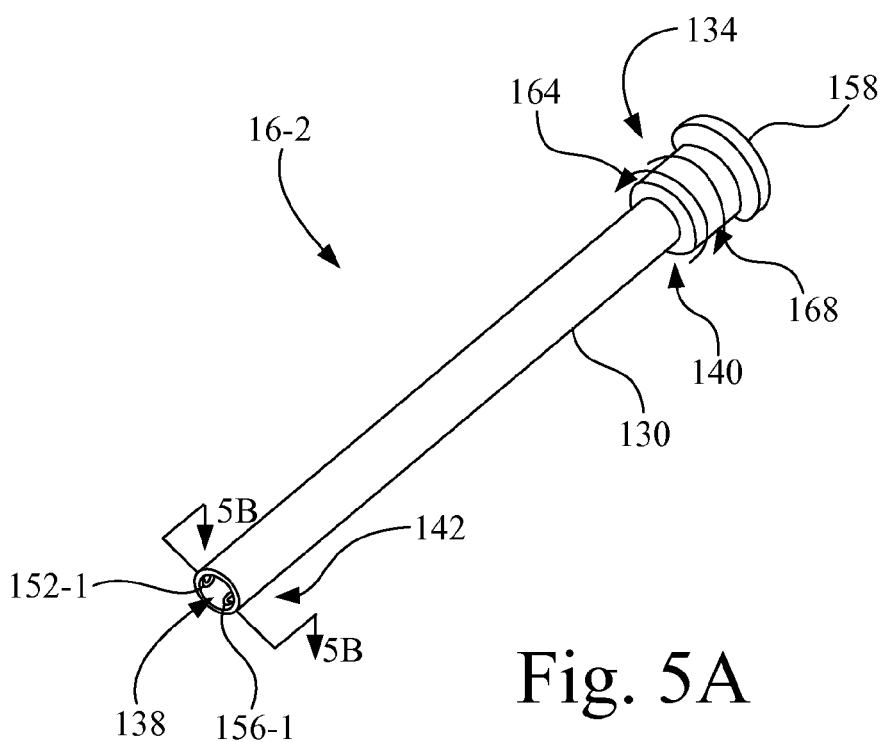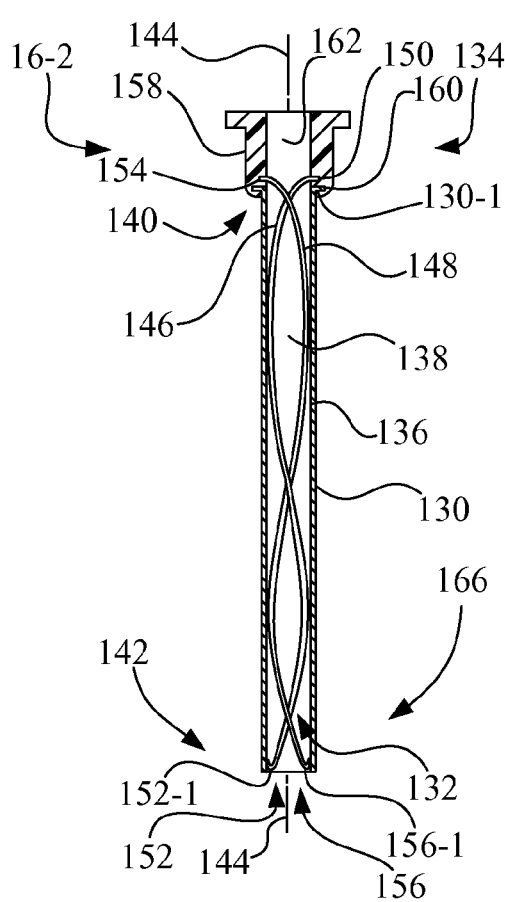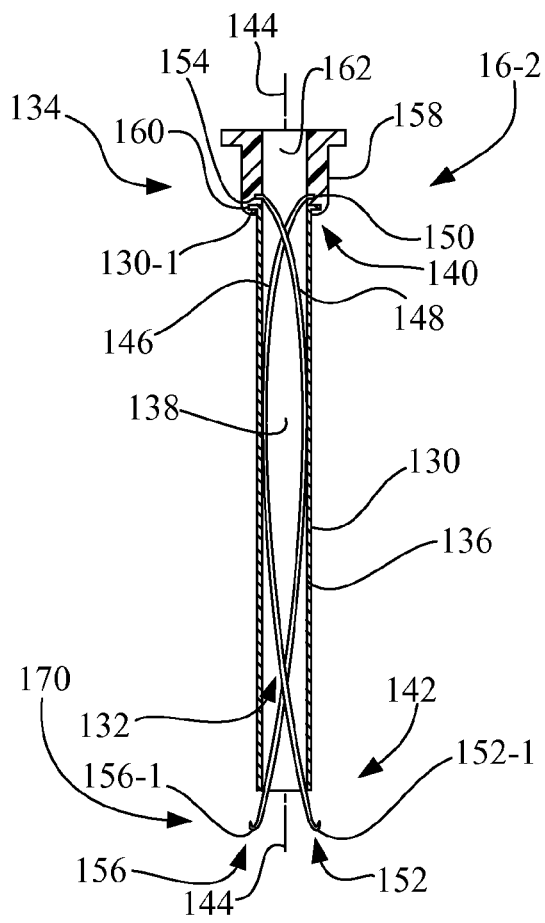
Fig. 5A
Fig. 5B
Fig. 5C

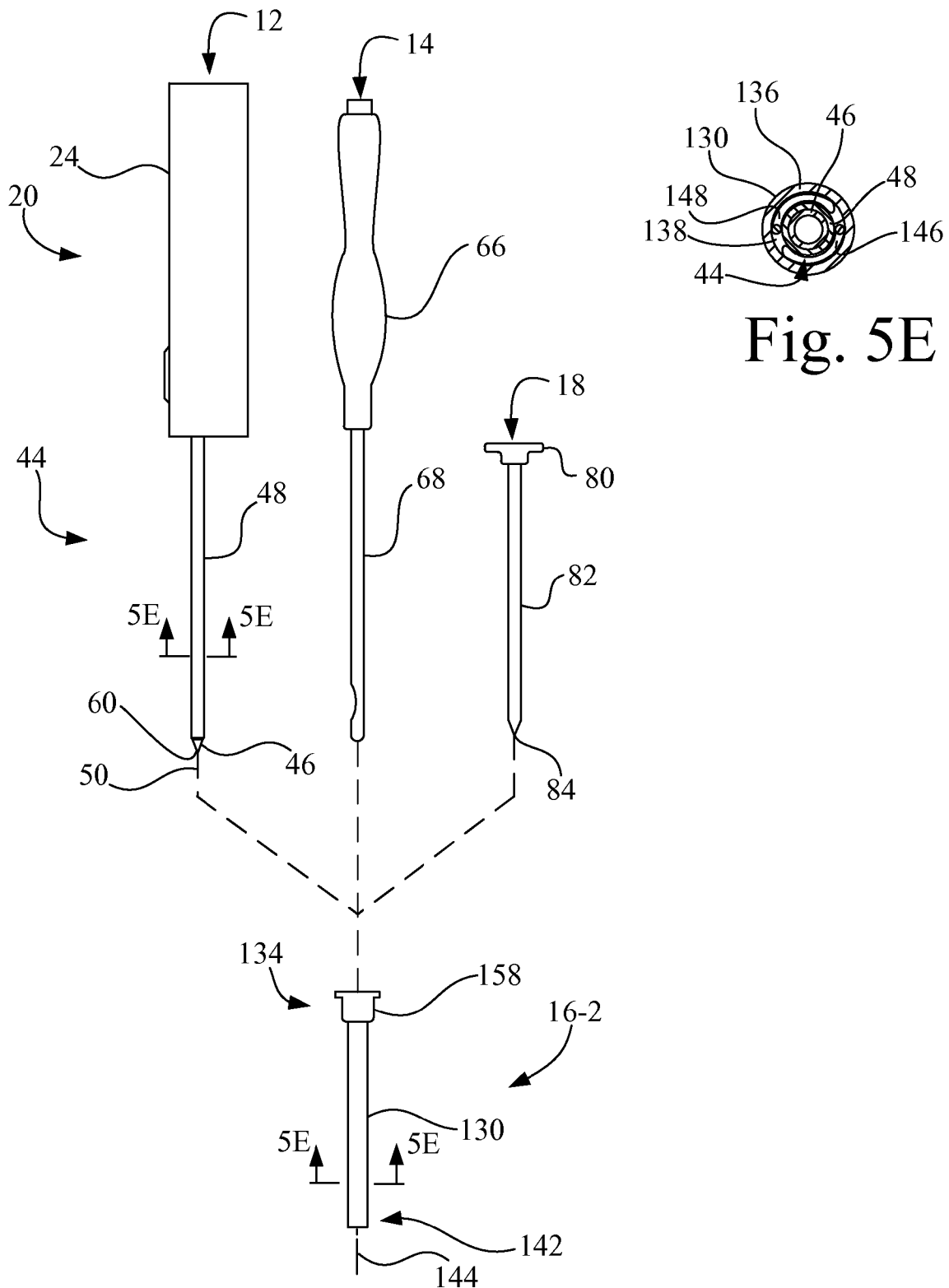

INTRODUCER CANNULA HAVING A TISSUE ANCHOR FOR USE WITH A MEDICAL INSTRUMENT

CROSS-REFERENCE TO RELATED APPLICATIONS

None.

MICROFICHE APPENDIX

None.

GOVERNMENT RIGHTS IN PATENT

None.

BACKGROUND OF THE INVENTION

1. Field of the Invention

The present invention relates to a medical device, and, more particularly, to an introducer cannula having a tissue anchor, the introducer cannula being configured for use with a medical instrument.

2. Description of the Related Art

A biopsy may be performed on a patient to help in determining whether the cells in a tissue lesion to be biopsied are cancerous. A typical biopsy apparatus includes a hand-held driver assembly having one or more drivers that drivably engage driven components of a disposable biopsy probe mechanism configured for releasable attachment to the driver assembly. The biopsy probe mechanism typically includes a biopsy cannula, e.g., a needle, having a sample port for receiving the tissue to be sampled, and a cutting cannula for severing tissue received in the sample port.

For surgical biopsies, the physician may introduce a localization ("loc") wire under image guidance, which anchors to the target lesion and provides a physical pathway to the biopsy site for subsequent surgery. The loc wire features hooks and/or other geometries to anchor to the tissue.

In some circumstances, an introducer cannula may be used to aid in maintaining an access pathway to the tissue lesion. The pathway may be used to for obtaining tissue samples via the biopsy apparatus and for subsequently introducing a tissue marker. However, problems may be experienced if the introducer cannula used to maintain the access pathway to the tissue lesion undergoes migration, which as a result would require the physician to reposition the introducer cannula to avoid the biopsy being performed at the wrong location or a tissue marker being deployed at the wrong location.

SUMMARY OF THE INVENTION

The present invention provides tissue anchoring features on an introducer cannula to aid in preventing migration of the introducer cannula for accurate positioning of a medical instrument, such as a biopsy probe of a biopsy apparatus or a marker cannula of a tissue marking apparatus.

The invention, in one form thereof, is directed to an introducer cannula configured for receiving a medical instrument. The introducer cannula includes a cannula tube having a side wall, a proximal end, and a distal end, and the side wall surrounding a central lumen. The cannula tube has a central longitudinal axis passing through the central lumen and extends between the proximal end and the distal end. An elongate tissue anchor is positioned in the central lumen of the cannula tube. The elongate tissue anchor has a mounting end and an anchoring free end. The elongate tissue anchor is movable in the central lumen such that the anchoring free end is movable between a retracted position and a deployed position. An actuator is coupled to the proximal end of the cannula tube. The actuator is coupled to the mounting end of the elongate tissue anchor. The actuator is operatively configured to selectively position the anchoring free end of the elongate tissue anchor in one of the retracted position and the deployed position.

The invention, in another form thereof, is directed to a biopsy system. The biopsy system includes a medical instrument and an introducer cannula configured for receiving the medical instrument. The introducer cannula includes a cannula tube having a side wall, a proximal end, and a distal end, and the side wall surrounding a central lumen. An elongate tissue anchor is positioned in the central lumen of the cannula tube. The central lumen is sized to concurrently accommodate both the elongate tissue anchor and a portion of the medical instrument. The elongate tissue anchor has a mounting end and an anchoring free end. The elongate tissue anchor is movable in the central lumen such that the anchoring free end is movable between a retracted position and a deployed position. An actuator is coupled to the proximal end of the cannula tube. The actuator is coupled to the mounting end of the elongate tissue anchor. The actuator is operatively configured to selectively position the anchoring free end of the elongate tissue anchor in one of the retracted position and the deployed position.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 5A is a perspective view of another embodiment of the introducer cannula of FIG. 1;

FIG. 5B a is section view of the embodiment of the introducer cannula of FIG. 5A taken along line 5B-5B, with the anchoring free ends of the elongate tissue anchor in a retracted position;

FIG. 5C is section view of the embodiment of the introducer cannula of FIG. 5A taken along line 5B-5B, with the anchoring free ends of the elongate tissue anchor in a deployed position;

FIG. 5D is a pictorial illustration of the use of the biopsy apparatus, marking apparatus, introducer cannula and stylet of FIG. 1 with the introducer cannula of FIGS. 5A-5C; and FIG. 5E is a section view of the cannula tube of the introducer cannula of FIG. 5D taken along line 5E-5E when the biopsy probe of the biopsy apparatus is inserted in the lumen of the cannula tube of the introducer cannula, concurrently with the elongate tissue anchor.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION OF THE INVENTION

Figure 1:
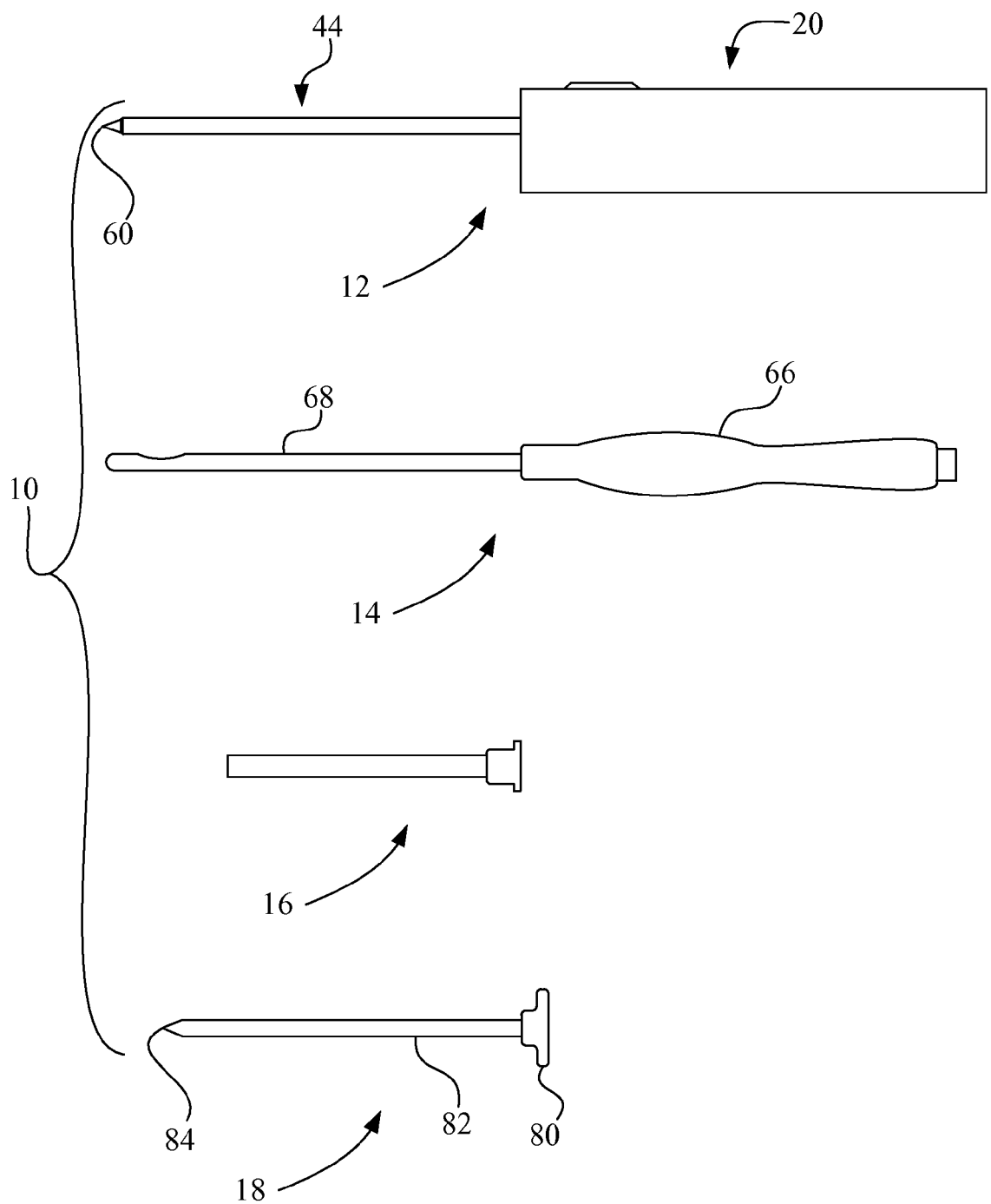
FIG. 1 illustrates an exemplary biopsy system kit that includes a biopsy apparatus, a marking apparatus, an introducer cannula and a stylet.

Referring now to the drawings, and more particularly to FIG. 1, there is shown an exemplary biopsy system kit 10, which may include, for example, a biopsy apparatus 12, a marking apparatus 14, an introducer cannula 16 and a stylet 18. Biopsy apparatus 12 is used to perform a biopsy procedure on a patient. Following a biopsy procedure, a physician may mark the biopsy site with a tissue marker, which may be deployed, for example, using marking apparatus 14.

Introducer cannula 16 is provided to aid in the transition from the biopsy apparatus 12 to marking apparatus 14, and to aid in the positioning of either of biopsy apparatus 12 or marking apparatus 14. As will be described in more detail below, introducer cannula 16 may be inserted into the patient during insertion of the probe portion of biopsy apparatus 12 into the patient, or alternatively, may be inserted into the patient with the aid of the removable stylet 18. In any event, introducer cannula 16 may be used to maintain an access pathway to the tissue lesion and/or biopsy site in the patient.

Figure 2:
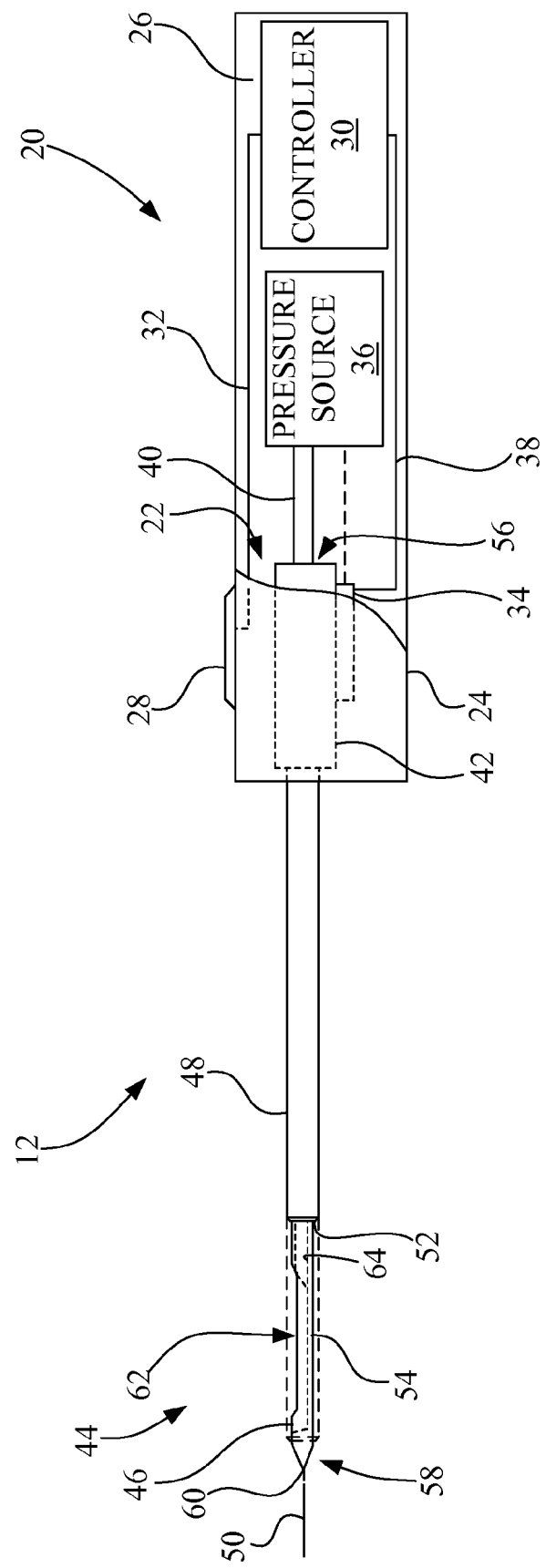
FIG. 2 is a side view of the biopsy apparatus of FIG. 1 having a biopsy probe mechanism mounted to a biopsy driver assembly, and with a side portion broken away on the biopsy driver assembly to expose internal components which are schematically represented in part.

Referring to FIG. 2, biopsy apparatus 12 includes a driver assembly 20 and a biopsy probe mechanism 22. Driver assembly 20 is configured to provide operative control over biopsy probe mechanism 22. Driver assembly 20 includes a housing 24 configured, e.g., ergonomically designed, to be grasped by a user, e.g., a physician. Housing 24 defines a compartment 26 into which biopsy probe mechanism 22 is at least partially positioned when biopsy probe mechanism 22 is attached to driver assembly 20, with biopsy probe mechanism 22 being drivably coupled to driver assembly 20.

Driver assembly 20 further includes a user interface 28 located to be externally accessible to the user with respect to housing 24 for receiving operation commands from the user, e.g., through one or more pushbuttons, and may also include a display, e.g., one or more lights or an LCD (liquid crystal display), to display information to the user. A controller 30 is communicatively coupled user interface 28 via a communication link 32, such as for example, wire cabling, printed circuits, etc. Controller 30 may include, for example, a microprocessor and associated memory (not shown) for executing program instructions to perform functions associated with the harvesting of biopsy tissue samples during a biopsy procedure.

There is contained within housing 24 an electromechanical drive 34 and a pressure source 36. Electromechanical drive 34 is connected in electrical communication with controller 30 via a communication link 38, such as for example, wire cabling, printed circuits, etc. Electromechanical drive 34 is further drivably coupled (illustrated by dashed lines) to the biopsy probe mechanism 22 and to the pressure source 36 to selectively and operatively control biopsy probe mechanism 22 and pressure source 36. Electromechanical drive 34 may include, for example, one or more of a linear drive that converts rotational motion to linear motion (e.g., a worm gear arrangement, rack and pinion arrangement, solenoid-slide arrangement, etc.) and a rotational drive that may include one or more of a gear, gear train, belt/pulley arrangement, etc., for effecting operation of biopsy probe mechanism 22 and/or pressure source 36.

Pressure source 36 may be, for example, a peristaltic pump, a diaphragm pump, syringe-type pump, etc. Pressure source 36 may be permanently integrated into driver assembly 20, or alternatively may be permanently integrated as a part of the biopsy probe mechanism 22. In either case, pressure source 36 is coupled in fluid communication with biopsy probe mechanism 22, e.g., via conduit 40, and is configured to generate negative pressure (vacuum), and in some embodiments may also generate positive pressure.

Biopsy probe mechanism 22 is generally intended to be disposable as a unit and intended for use on a single patient. Biopsy probe mechanism 22 includes a frame 42 to which is attached a biopsy probe 44. Biopsy probe 44 includes a sample receiving member 46 and a cutting cannula 48. Sample receiving member 46 and a cutting cannula 48 are arranged coaxially with respect to a longitudinal axis 50. Cutting cannula 48 has a distal cutting edge 52. Sample receiving member 46 and a cutting cannula 48 are mounted as a coaxial unit to frame 42.

In the present embodiment, sample receiving member 46 may be formed, for example, as an elongate cylindrical tube 54 having a proximal end 56 and a distal end 58. Sample receiving member 46 may be made, for example, from a metal, such as stainless steel, titanium, or a nickel alloy. In the present embodiment, distal end 58 has a piercing tip 60. Longitudinal axis 50 extends between proximal end 56 and distal end 58.

A sample receiving notch 62 is formed in sample receiving member 46, e.g., by machining a portion of a sample receiving notch 62 of sample receiving member 46 and extends into a lumen 64 of sample receiving member 46 (shown by dashed lines). Sample receiving notch 62 is configured to receive the tissue to be biopsied, and to retain the tissue sample harvested from the tissue, during a biopsy procedure. Sample receiving notch 62 may be also sometimes referred to as a sample chamber. Sample receiving notch 62 in sample receiving member 46 is coupled in fluid communication with pressure source 36 via conduit 40. It is to be understood, however, that some designs of biopsy apparatus 12 may not utilize a pressure source.

In preparation for insertion of biopsy probe 44 of biopsy probe mechanism 22 into introducer cannula 16, for example, cutting cannula 48 is controlled by controller 30 and electromechanical drive 34 to translate linearly along longitudinal axis 50 to cover sample receiving notch 62 (shown in phantom lines in FIG. 2) of sample receiving member 46. In operation, a user may use piercing tip 60 of biopsy probe 44 to establish an access pathway through tissue to a biopsy site, with biopsy probe 44 having been inserted through introducer cannula 16.

After insertion of biopsy probe 44 into the patient at the desired location, cutting cannula 48 is controlled by controller 30 and electromechanical drive 34 to translate linearly along longitudinal axis 50 to expose sample receiving notch 62 (shown in solid lines in FIG. 2) to receive a tissue sample, and thereafter is controlled to cause cutting cannula 48 to translate linearly along longitudinal axis 50 during a linear advancement to cover sample receiving notch 62 (shown in phantom lines in FIG. 2) and sever the tissue in sample receiving notch 62. Also, cutting cannula 48 may be controlled to rotate or oscillate with, or independent from, any linear advancement of cutting cannula 48.

Thereafter, biopsy probe 44 may be withdrawn from introducer cannula 16, and in turn withdrawn from the patient, while introducer cannula 16 remains in the tissue of the patient to maintain the access pathway and to maintain the location of the biopsy site.

Figure 3:
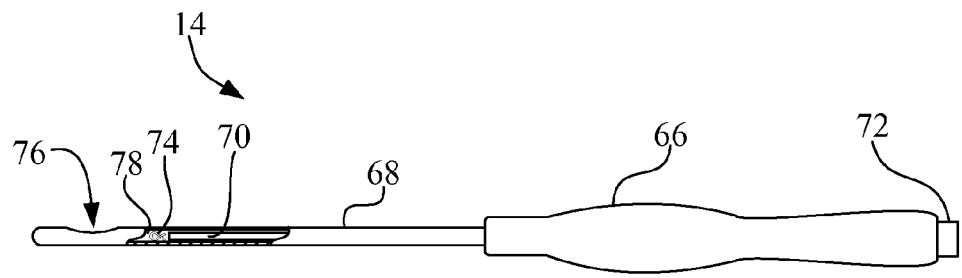
FIG. 3 is a side view of the marking apparatus of FIG. 1, with a portion of the cannula broken away to expose the marker introducer rod and marker contained the cannula.

Referring to FIG. 3, marking apparatus 14 includes a handle 66, a marker cannula 68, a marker introducer rod 70, and a deployment mechanism 72. Handle 66 is configured to be grasped by a user, i.e., is of an appropriate size and shape to be grasped by the hand of the user of marking apparatus 14. Deployment mechanism 72 is operatively coupled to marker introducer rod 70. Marker cannula 68 is configured for holding at least one tissue marker 74 for deployment into a tissue mass of a patient, and may be in the form of a hollow tube having a side port 76 (or alternatively an end port) leading into a lumen 78 in which tissue marker 74 is located. Also positioned for linear travel in lumen 78 is marker introducer rod 70.

In operation, a user positions marking apparatus 14 by inserting marker cannula 68 into a prepositioned introducer cannula 16. Once the marking apparatus is in the proper position, a user then depresses deployment mechanism 72, which in turn advances marker introducer rod 70 to deploy tissue marker 74 out of side port 76.

Referring again to FIGS. 1 and 2, as an alternative to using the piercing tip 60 of biopsy probe 44 to establish the access pathway through tissue of the patient, stylet 18 may be used for this purpose. Stylet 18 includes a handle 80 fixedly attached to a shaft 82, with shaft 82 having a piercing tip 84 at an end opposite to handle 80. In operation, a user may use piercing tip 84 of shaft 82 to establish a pathway through tissue to a biopsy site, with shaft 82 of stylet 18 having been inserted through introducer cannula 16. Thus, stylet 18 may be used to position introducer cannula 16 in tissue of a patient, independent of biopsy apparatus 12 and/or marking apparatus 14.

Referring to FIGS. 4A-4E there is shown an embodiment of introducer cannula 16, hereinafter referred to as introducer cannula 16-1. Introducer cannula 16-1 includes a cannula tube 90, an elongate tissue anchor 92, and an actuator 94.

Figure 4A:
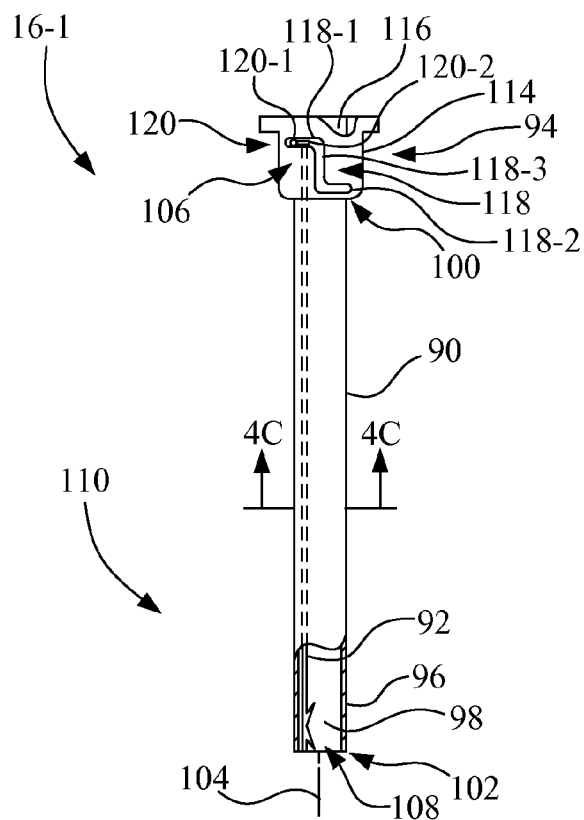
FIG. 4A is a side view of an embodiment of the introducer cannula of FIG. 1, with an upper portion broken away to show a hollow interior of the hub, and a lower portion sectioned away to expose the anchoring free end of the elongate tissue anchor in a retracted position.
Figure 4B:
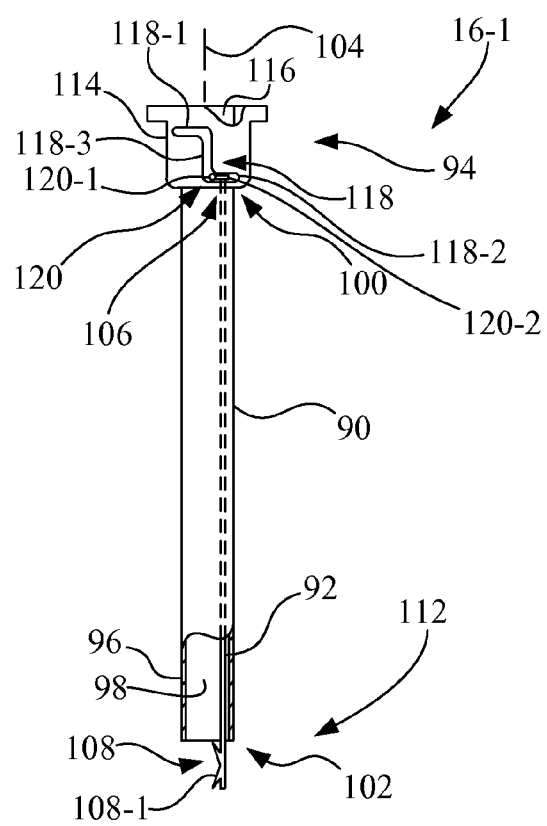
FIG. 4B is a side view of an embodiment of the introducer cannula of FIG. 1, with an upper portion broken away to show a hollow interior of the hub, and a lower portion sectioned away to expose the central lumen, and with the anchoring free end of the elongate tissue anchor in a deployed position.
Figure 4C:
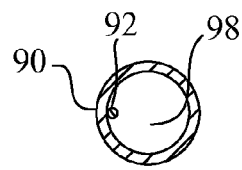
FIG. 4C is a section view of the cannula tube of the introducer cannula of FIG. 4A taken along line 4C-4C.
Figures 4D, 4E:
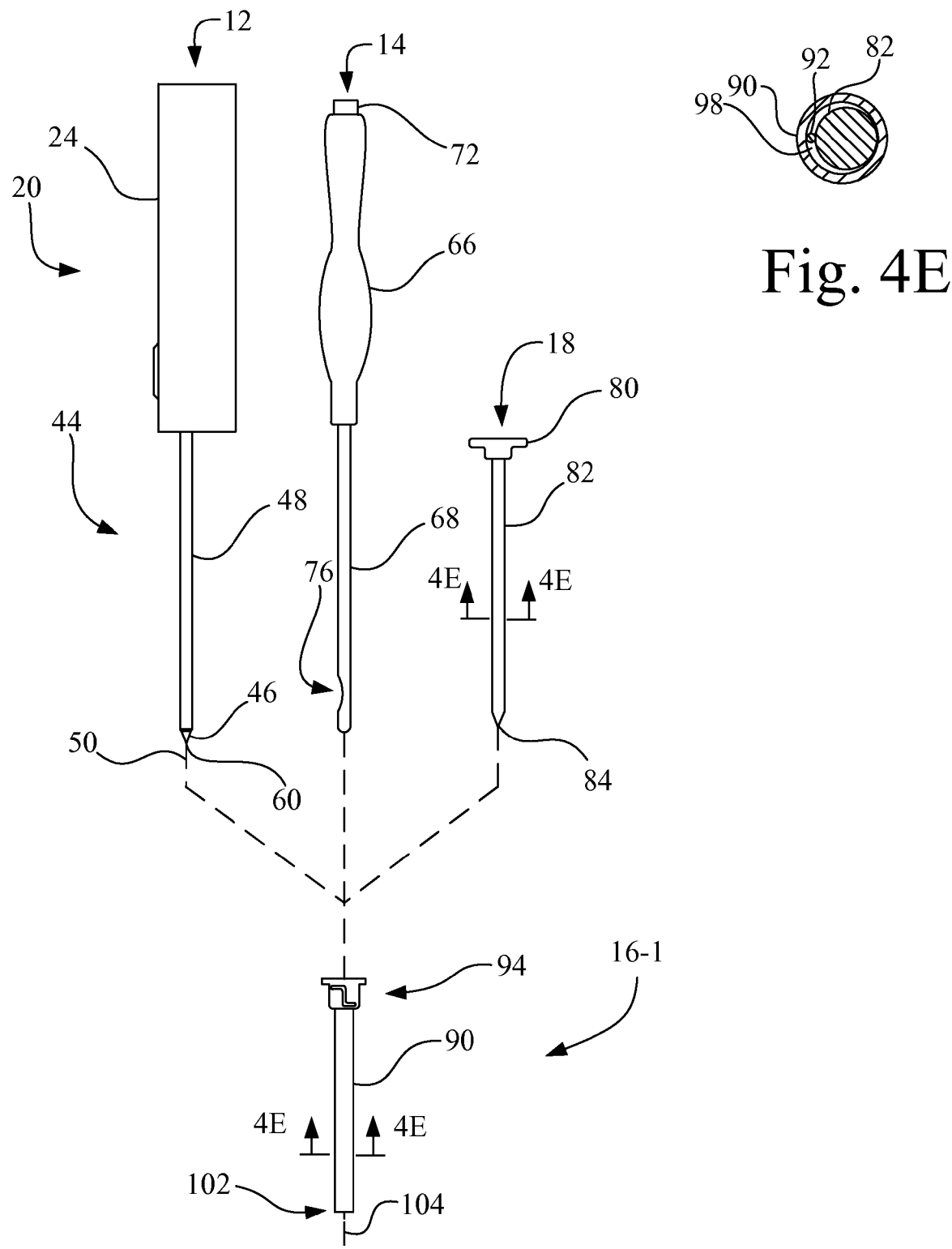
FIG. 4D is a pictorial illustration of the use of the biopsy apparatus, marking apparatus, introducer cannula and stylet of FIG. 1 with the introducer cannula of FIGS. 4A and 4B.
FIG. 4E is a section view of the cannula tube of the introducer cannula of FIG. 4D taken along line 4E-4E when the stylet is inserted in the lumen of the cannula tube of the introducer cannula, concurrently with the elongate tissue anchor.

Cannula tube 90 has a side wall 96 surrounding a central lumen 98, a proximal end 100, and a distal end 102. Cannula tube 90 has a central longitudinal axis 104 passing through central lumen 98 that extends between proximal end 100 and distal end 102. As illustrated in FIGS. 4C-4E, a cross section of central lumen 98 is sized to concurrently accommodate both elongate tissue anchor 92 and one of biopsy probe 44 of biopsy apparatus 12, marker cannula 68 of marking apparatus 14, and shaft 82 of stylet 18. Cannula tube 90 is substantially rigid, and may be made, for example, from a metallic material, such as for example, stainless steel, nitinol, a nickel-chromium alloy, titanium, etc. As used immediately above, the term "substantially rigid" refers to structure that exhibits little, if any, radial deflection relative to central longitudinal axis 104 in normal use.

Referring again to FIGS. 4A-4C, elongate tissue anchor 92 is positioned in central lumen 98 of cannula tube 90. Elongate tissue anchor 92 has a mounting end 106 and an anchoring free end 108. Anchoring free end 108 of elongate tissue anchor 92 may include a pair of barbs 108-1 spaced apart along a longitudinal extent of elongate tissue anchor 92, or some other anchoring configuration, such as a hook. Elongate tissue anchor 92 may be configured to be flexible, while exhibiting little or no permanent deformation during normal use. Elongate tissue anchor 92 may be formed, for example, as a wire or rod made of metallic material, such as for example, stainless steel, a nickel-chromium alloy, titanium, etc, and in some embodiments may be formed from a "memory" material, such as nitinol.

Anchoring free end 108 of elongate tissue anchor 92 is movable in central lumen 98 between a retracted position 110 and a deployed position 112. When anchoring free end 108 of elongate tissue anchor 92 is in retracted position 110, for example, anchoring free end 108 is completely contained within central lumen 98 proximal to distal end 102 of cannula tube 90. When anchoring free end 108 of elongate tissue anchor 92 is in deployed position 112, anchoring free end 108 is completely exposed external to central lumen 98 distal to distal end 102 of cannula tube 90.

Actuator 94 is coupled to proximal end 100 of cannula tube 90. Actuator 94 is also coupled to mounting end 106 of elongate tissue anchor 92. Actuator 94 is operatively configured to selectively position anchoring free end 108 of elongate tissue anchor 92 in one of the retracted position 110 and the deployed position 112.

More particularly, in the present embodiment actuator 94 includes a hub 114 fixedly connected to proximal end 100 of cannula tube 90. Hub 114 has a hollow interior 116 coaxial with central lumen 98 with respect to central longitudinal axis 104. Hub 114 has a guide slot 118 having a proximal circumferential slotted portion 118-1, a distal circumferential slotted portion 118-2, and a longitudinal portion 118-3 extending between proximal circumferential slotted portion 118-1 and distal circumferential slotted portion 118-2. Proximal circumferential slotted portion 118-1 defines the retracted position 110 and distal circumferential slotted portion 118-2 defines the deployed position 112, with the longitudinal extent of longitudinal portion 118-3 defining the longitudinal distance traveled by anchoring free end 108 when moved from retracted position 110 to deployed position 112.

An actuation lever 120 is mounted in guide slot 118. Actuation lever 120 has a first end 120-1 and a second end 120-2. The first end 120-1 is positioned to extend outwardly from guide slot 118. The second end 120-2 is positioned in hollow interior 116 and is connected to the mounting end 106 of elongate tissue anchor 92. Accordingly, movement of actuation lever 120 along guide slot 118 results in a corresponding movement of elongate tissue anchor 92. Elongate tissue anchor 92 extends from mounting end 106 connected to actuation lever for substantially a full longitudinal extent of cannula tube 90 to anchoring free end 108. As used immediately above, the term "substantially" refers to a range of 90 percent to 100 percent of the extent of cannula tube 90.

Referring to FIGS. 4D and 4E, introducer cannula 16-1 is configured to removably receive a portion of a medical instrument, such as biopsy probe 44 of biopsy apparatus 12, marker cannula 68 of marking apparatus 14, or shaft 82 of stylet 18. More particularly, for example, cannula tube 90 is configured in cross sectional size and shape to removably receive the portion of the medical instrument in central lumen 98 in cannula tube 90 concurrently with, and immediately adjacent to, elongate tissue anchor 92 in central lumen 98.

To establish a pathway in tissue of a patient, for example, one of the piercing tip 60 of biopsy probe 44 or piercing tip 84 of stylet 18 may be used. In the first instance, biopsy probe 44 is inserted though central lumen 98 of cannula tube 90, with piercing tip 60 extending beyond distal end 102 of cannula tube 90. In the instance of stylet 18, shaft 82 of stylet 18 is inserted though central lumen 98 of cannula tube 90, with piercing tip 84 extending beyond distal end 102 of cannula tube 90. Thus, either of biopsy probe 44 of biopsy apparatus 12 or stylet 18 may be used to establish an access pathway and position introducer cannula 16-1 in tissue of a patient.

Thereafter, actuator 94 of introducer cannula 16-1 is actuated to deploy anchoring free end 108 of elongate tissue anchor 92 to the deployed position 112 at which time anchoring free end 108 of elongate tissue anchor 92 engages the tissue of the patient to anchor introducer cannula 16-1 to the tissue of the patient and maintain the access pathway in the tissue of the patient established by the piercing tip (e.g., one of piercing tip 60 of biopsy probe 44 or piercing tip 84 of stylet 18). Once anchored, introducer cannula 16-2 permits a respective medical instrument, e.g., biopsy apparatus 12, to be removed from the anchored introducer cannula 16-1 and reinserted in the patient while maintaining the established access pathway. Additionally, the anchored introducer cannula 16-2 permits a respective medical instrument, e.g., biopsy apparatus 12, to be removed from the anchored introducer cannula 16-1 and replaced with a medical instrument of a different type, e.g., marking apparatus 14, for performing a different procedure using the same access pathway in the tissue maintained by the anchored introducer cannula 16-1.

After all medical procedures involving introducer cannula 16-1 have been completed, then introducer cannula 16-1 may be removed from the patient by first retracting elongate tissue anchor 92 to the retracted position 110, and then removing cannula tube 90 from the tissue of the patient.

Referring to FIGS. 5A-E there is shown another embodiment of introducer cannula 16, hereinafter referred to as introducer cannula 16-2. Introducer cannula 16-2 includes a cannula tube 130, an elongate tissue anchor 132, and an actuator 134.

Cannula tube 130 has a side wall 136 surrounding a central lumen 138, a proximal end 140, and a distal end 142. Cannula tube 130 has a central longitudinal axis 144 passing through central lumen 138 that extends between proximal end 140 and distal end 142. As illustrated in FIG. 5E with reference to FIG. 5D, a cross section of central lumen 138 is sized to concurrently accommodate both elongate tissue anchor 132 and one of biopsy probe 44 of biopsy apparatus 12, marker cannula 68 of marking apparatus 14, and shaft 82 of stylet 18. Cannula tube 130 is substantially rigid, and may be made, for example, from a metallic material, such as for example, stainless steel, nitinol, a nickel-chromium alloy, titanium, etc. As used immediately above, the term "substantially rigid" refers to structure that exhibits little, if any, radial deflection relative to central longitudinal axis 144 in normal use.

Elongate tissue anchor 132 is positioned in central lumen 138 of cannula tube 130. In the present embodiment, elongate tissue anchor 132 is formed as a plurality of individual elongate anchor elements which number as two in the exemplary embodiment shown in FIGS. 5A-5E, and which are individually identified as elongate anchor element 146 and elongate anchor element 148. Each of elongate anchor elements 146, 148 is configured to be flexible, while exhibiting little or no permanent deformation during normal use. Each of elongate anchor elements 146, 148 has an actual length that is longer than the longitudinal extent in the direction of longitudinal axis 144 of cannula tube 130. Each of elongate anchor elements 146, 148 is formed in a spiral and is positioned in central lumen 138 to frictionally engage the side wall 136 of cannula tube 130. Elongate tissue anchor 92 may be formed, for example, as a wire made of metallic material, such as for example, stainless steel, a nickel-chromium alloy, titanium, etc, and in some embodiments may be formed from a "memory" material, such as nitinol.

Elongate anchor element 146 has a mounting end 150 and an anchoring free end 152. Elongate anchor element 148 has a mounting end 154 and an anchoring free end 156. The mounting end 150 of elongate anchor element 146 and the mounting end 154 of elongate anchor element 148 are respectively connected to actuator 134 in an opposing relationship. Anchoring free end 152 of elongate anchor element 146 may be in the form of a sharpened hooked end 152-1, or alternatively some other anchoring structure, such as a barb. Anchoring free end 156 of elongate anchor element 148 may be in the form of a sharpened hooked end 156-1, or alternatively some other anchoring structure, such as a barb.

Actuator 134 includes a hub 158 rotatably coupled to proximal end 140 of cannula tube 130. Hub 158 includes an annular channel 160 in which an annular flange 130-1 of cannula tube 130 is rotatably engaged. Hub 158 has a hollow interior 162 coaxial with central lumen 138. The respective mounting ends 150, 154 of each of elongate anchor elements 146, 148 of elongate tissue anchor 132 are connected to hub 158 in an opposing relationship, e.g., at opposite sides of hub 158, in hollow interior 162. Each of elongate anchor elements 146, 148 of elongate tissue anchor 132 form a spiral (i.e., coil-like) shape within central lumen 138 of cannula tube 130 with each of elongate anchor elements 146, 148 of elongate tissue anchor 132 being in frictional engagement with side wall 136 of cannula tube 130.

In operation, a rotation of hub 158 in a first rotational direction 164 moves the respective anchoring free ends 152, 156 of each of elongate anchor elements 146, 148 of elongate tissue anchor 132 toward a retracted position 166, and a rotation of hub 158 in a second rotational direction 168 opposite first rotational direction 164 moves anchoring free ends 152, 156 of each of elongate anchor elements 146, 148 of elongate tissue anchor 132 toward a deployed position 170. In other words, a rotation of hub 158 in the first rotational direction 164 moves the respective anchoring free ends 152, 156 of each of elongate anchor elements 146, 148 of elongate tissue anchor 132 toward the retracted position 166 by winding each of elongate anchor elements 146, 148 of elongate tissue anchor 132 within central lumen 138 of cannula tube 130 to decrease the effective length of each of elongate anchor elements 146, 148 of elongate tissue anchor 132 relative to longitudinal extent of cannula tube 130. Conversely, and a rotation of hub 158 in the second rotational direction 168 opposite first rotational direction 164 moves anchoring free ends 152, 156 of each of elongate anchor elements 146, 148 of elongate tissue anchor 132 toward a deployed position 170 by unwinding each of elongate anchor elements 146, 148 of elongate tissue anchor 132 within central lumen 138 of cannula tube 130 to increase the effective length of each of elongate anchor elements 146, 148 of elongate tissue anchor 132 relative to longitudinal extent of cannula tube 130.

Referring to FIGS. 5D and 5E, introducer cannula 16-2 is configured to removably receive a portion of a medical instrument, such as biopsy probe 44 of biopsy apparatus 12, marker cannula 68 of marking apparatus 14, or shaft 82 of stylet 18.

More particularly, for example, cannula tube 130 is configured in cross sectional size and shape to removably receive the portion of the medical instrument, e.g., biopsy probe 44, in central lumen 138 in cannula tube 130 concurrently with, and immediately adjacent to, elongate tissue anchor 132 (e.g., elongate anchor elements 146, 148) in central lumen 98.

To establish a pathway in tissue of a patient, for example, one of the piercing tip 60 of biopsy probe 44 or piercing tip 84 of stylet 18 may be used. In the first instance, biopsy probe 44 is inserted though central lumen 138 of cannula tube 130, with piercing tip 60 extending beyond distal end 142 of cannula tube 130. In the instance of stylet 18, shaft 82 of stylet 18 is inserted though central lumen 138 of cannula tube 130, with piercing tip 84 extending beyond distal end 142 of cannula tube 90. Thus, either of biopsy probe 44 of biopsy apparatus 12 or stylet 18 may be used to establish an access pathway and position introducer cannula 16-2 in tissue of a patient.

Thereafter, actuator 134 of introducer cannula 16-2 is actuated to deploy anchoring free ends 152, 156 of elongate anchor elements 146, 148 forming elongate tissue anchor 132 to the deployed position 170 at which time anchoring free ends 152, 156 of elongate anchor elements 146, 148 forming elongate tissue anchor 132 engage the tissue of the patient to anchor introducer cannula 16-2 to the tissue of the patient and maintain the access pathway in the tissue of the patient established by the piercing tip (e.g., one of piercing tip 60 of biopsy probe 44 or piercing tip 84 of stylet 18).

Once anchored, introducer cannula 16-2 permits a respective medical instrument, e.g., biopsy apparatus 12, to be removed from the anchored introducer cannula 16-2 and reinserted in the patient while maintaining the established pathway. Additionally, the anchored introducer cannula 16-2 permits a respective medical instrument, e.g., biopsy apparatus 12, to be removed from the anchored introducer cannula 16-2 and replaced with a medical instrument of a different type, e.g., marking apparatus 14, for performing a different procedure using the same access pathway in the tissue maintained by the anchored introducer cannula 16-2.

After all medical procedures involving introducer cannula 16-2 have been completed, then introducer cannula 16-2 may be removed from the patient by first retracting anchoring free ends 152, 156 of elongate anchor elements 146, 148 forming elongate tissue anchor 132 to the retracted position 166, and then removing cannula tube 130 from the tissue of the patient.

Thus, in summary, in accordance with an aspect of the present invention, the introducer cannula 16 (e.g., 16-1, 16-2) includes a retractable/deployable elongate tissue anchor to aid in preventing migration of the introducer cannula 16 in a patient. The anchored introducer cannula 16 facilitates the accurate positioning in the patient of one or more medical instruments, such as a biopsy probe 44 of a biopsy apparatus 12 or a marker cannula 68 of tissue marking apparatus 14. Advantageously, the introducer cannula 16 may be anchored to the tissue of a patient to maintain an access pathway in the tissue, while the respective medical instrument may be removed from and re-installed in the same access pathway in the tissue via the anchored introducer cannula 16. Similarly, a respective medical instrument may be removed from the anchored introducer cannula 16 and replaced with a medical instrument of a different type for performing a different procedure using the same access pathway in the tissue maintained by the anchored introducer cannula 16. After all medical procedures have been completed, introducer cannula 16 then may be removed from the patient by retracting the elongate tissue anchor and sliding the introducer cannula out of the access pathway in the patient.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An introducer cannula configured for receiving a medical instrument, comprising:
   a cannula tube having a side wall, a proximal end, and a distal end, said side wall surrounding a central lumen, said cannula tube having a central longitudinal axis passing through said central lumen and extending between said proximal end and said distal end;
   an elongate tissue anchor positioned in said central lumen of said cannula tube, said elongate tissue anchor having a mounting end and an anchoring free end, said elongate tissue anchor being movable in said central lumen such that said anchoring free end is movable between a retracted position and a deployed position; and
   an actuator coupled to said proximal end of said cannula tube, said actuator being coupled to said mounting end of said elongate tissue anchor, said actuator being operatively configured to rotate relative to the cannula tube to selectively position said anchoring free end of said elongate tissue anchor in one of said retracted position and said deployed position.

2. The introducer cannula of claim 1, wherein said actuator includes a hub rotatably coupled to said proximal end of said cannula tube, said hub having a hollow interior coaxial with said central lumen, said mounting end of said elongate tissue anchor being connected to said hub, said elongate tissue anchor configured to form a spiral shape within said central lumen of said cannula tube, and the actuator is configured such that a rotation of said hub in a first rotational direction moves said anchoring free end of said elongate tissue anchor toward said retracted position, and the actuator is configured such that a rotation of said hub in a second rotational direction opposite said first rotational direction moves said anchoring free end of said elongate tissue anchor toward said deployed position.

3. The introducer cannula of claim 2, wherein said elongate tissue anchor includes a plurality of elongate anchor elements, each of said plurality of elongate anchor elements being formed in a spiral and positioned in said lumen to frictionally engage said side wall of said cannula tube.

4. The introducer cannula of claim 3, wherein said plurality of elongate anchor elements includes a first elongate anchor element and a second elongate anchor element, wherein said mounting end of said first elongate anchor element and said second elongate anchor element are respectively connected at opposite sides of said hub in said hollow interior.

5. The introducer cannula of claim 4, wherein said anchoring free end of each of said plurality of elongate anchor elements has a sharpened hooked end.

6. The introducer cannula of claim 1, wherein said actuator includes a hub rotatably coupled to said proximal end of said cannula tube, said hub having a hollow interior coaxial with said central lumen, said mounting end of said elongate tissue anchor being connected to said hub, said elongate tissue anchor being configured to form a spiral shape within said central lumen of said cannula tube with said elongate tissue anchor being in frictional engagement with said side wall of said cannula tube.

7. The introducer cannula of claim 6, wherein the actuator is configured such that a rotation of said hub in a first rotational direction moves said anchoring free end of said elongate tissue anchor toward said retracted position by winding said elongate tissue anchor within said central lumen, and the actuator is configured such that a rotation of said hub in a second rotational direction opposite said first rotational direction moves said anchoring free end of said elongate tissue anchor toward said deployed position by unwinding said elongate tissue anchor from within said central lumen.

8. An introducer cannula configured for receiving a medical instrument, comprising:
a cannula tube having a side wall, a proximal end, and a distal end, said side wall surrounding a central lumen, said cannula tube having a central longitudinal axis passing through said central lumen and extending between said proximal end and said distal end;
an elongate tissue anchor positioned in said central lumen of said cannula tube, said elongate tissue anchor having a mounting end and an anchoring free end, said elongate tissue anchor being movable in said central lumen such that said anchoring free end is movable between a retracted position and a deployed position; and
an actuator coupled to said proximal end of said cannula tube, said actuator being coupled to said mounting end of said elongate tissue anchor, said actuator being operatively configured to selectively position said anchoring free end of said elongate tissue anchor in one of said retracted position and said deployed position, wherein said actuator includes:
a hub fixedly connected to said end of said cannula tube, said hub having a hollow interior coaxial with said central lumen, said hub having a guide slot having a proximal circumferential slotted portion, a distal circumferential slotted portion, and a longitudinal portion extending between said proximal circumferential slotted portion and said distal circumferential slotted portion, said proximal circumferential slotted portion defining said retracted position and said distal circumferential slotted portion defining said deployed position; and
an actuation lever mounted in said guide slot, said actuation lever having a first end and a second end, said first end being positioned to extend outwardly from said guide slot, and said second end being positioned in said hollow interior and coupled to said mounting end of said elongate tissue anchor.

9. The introducer cannula of claim 8, wherein said elongate tissue anchor extends from said mounting end connected to said actuation lever for substantially a full longitudinal extent of said cannula tube to said anchoring free end.

10. A biopsy system, comprising:
a medical instrument; and
an introducer cannula configured for receiving the medical instrument, including:
a cannula tube having a side wall, a proximal end, and a distal end, said side wall surrounding a central lumen;
an elongate tissue anchor positioned in said central lumen of said cannula tube, said central lumen being sized to concurrently accommodate both said elongate tissue anchor and an elongate portion of said medical instrument, said elongate tissue anchor having a mounting end and an anchoring free end, said elongate tissue anchor being movable in said central lumen such that said anchoring free end is movable between a retracted position and a deployed position; and
an actuator coupled to said proximal end of said cannula tube, said actuator being coupled to said mounting end of said elongate tissue anchor, said actuator being operatively configured to rotate relative to the cannula tube to selectively position said anchoring free end of said elongate tissue anchor in one of said retracted position and said deployed position.

11. The biopsy system of claim 10, said elongate portion of said medical instrument being removably received in said central lumen of said introducer cannula concurrently with said elongate tissue anchor.

12. The biopsy system of claim 11, said medical instrument having a piercing tip to establish a pathway through tissue of a patient.

13. The biopsy system of claim 11, wherein said medical instrument is one of a biopsy apparatus, a marking apparatus and a stylet.

14. The biopsy system of claim 10, wherein said actuator includes a hub rotatably coupled to said proximal end of said cannula tube, said hub having a hollow interior coaxial with said central lumen, said mounting end of said elongate tissue anchor being connected to said hub, said elongate tissue anchor being configured to form a spiral shape within said central lumen of said cannula tube, and the actuator is configured such that a rotation of said hub in a first rotational direction moves said anchoring free end of said elongate tissue anchor toward said retracted position, and the actuator is configured such that a rotation of said hub in a second rotational direction opposite said first rotational direction moves said anchoring free end of said elongate tissue anchor toward said deployed position.

15. The biopsy system of claim 14, wherein said elongate tissue anchor includes a plurality of elongate anchor elements, each of said elongate anchor elements being formed in a spiral and positioned in said lumen to frictionally engage said side wall of said cannula tube.

16. The biopsy system of claim 15, wherein said plurality of elongate anchor elements includes a first elongate anchor element and a second elongate anchor element, wherein said mounting end of said first elongate anchor element and said second elongate anchor element are respectively connected at opposite sides of said hub in said hollow interior.

17. The biopsy system of claim 16, wherein said anchoring free end of each of said plurality of elongate anchor elements has a sharpened hooked end.

18. The biopsy system of claim 10, wherein said actuator includes a hub rotatably coupled to said proximal end of said cannula tube, said hub having a hollow interior coaxial with said central lumen, said mounting end of said elongate tissue anchor being connected to said hub, said elongate tissue anchor being configured to form a spiral shape within said central lumen of said cannula tube with said elongate tissue anchor being in frictional engagement with said side wall of said cannula tube.

19. The biopsy system of claim 18, wherein the actuator is configured such that a rotation of said hub in a first rotational direction moves said anchoring free end of said elongate tissue anchor toward said retracted position by winding said elongate tissue anchor within said central lumen, and the actuator is configured such that a rotation of said hub in a second rotational direction opposite said first rotational direction moves said anchoring free end of said elongate tissue anchor toward said deployed position by unwinding said elongate tissue anchor from within said central lumen.

20. A biopsy system, comprising:
a medical instrument; and
an introducer cannula configured for receiving the medical instrument, including:
  a cannula tube having a side wall, a proximal end, and a distal end, said side wall surrounding a central lumen;
  an elongate tissue anchor positioned in said central lumen of said cannula tube, said central lumen being sized to concurrently accommodate both said elongate tissue anchor and an elongate portion of said medical instrument, said elongate tissue anchor having a mounting end and an anchoring free end, said elongate tissue anchor being movable in said central lumen such that said anchoring free end is movable between a retracted position and a deployed position; and
  an actuator coupled to said proximal end of said cannula tube, said actuator being coupled to said mounting end of said elongate tissue anchor, said actuator being operatively configured to selectively position said anchoring free end of said elongate tissue anchor in one of said retracted position and said deployed position, wherein said actuator includes:
    a hub fixedly connected to said end of said cannula tube, said hub having a hollow interior coaxial with said central lumen, said hub having a guide slot having a proximal circumferential slotted portion, a distal circumferential slotted portion, and a longitudinal portion extending between said proximal circumferential slotted portion and said distal circumferential slotted portion, said proximal circumferential slotted portion defining said retracted position and said distal circumferential slotted portion defining said deployed position; and
    an actuation lever mounted in said guide slot, said actuation lever having a first end and a second end, said first end being positioned to extend outwardly from said guide slot, and said second end being positioned in said hollow interior and coupled to said mounting end of said elongate tissue anchor.

21. The biopsy system of claim 20, wherein said elongate tissue anchor extends from said mounting end connected to said actuation lever for substantially a full longitudinal extent of said cannula tube to said anchoring free end.

\* \* \* \* \*